United States Patent [19]

Lindemann

[11] Patent Number: 4,986,266
[45] Date of Patent: Jan. 22, 1991

[54] HEMI-ARM SLING WITH ABDUCTION CONTROL STRAP

[76] Inventor: Peer Lindemann, 338 Lagoon Dr., Ozona, Fla. 34660

[21] Appl. No.: 447,012

[22] Filed: Dec. 6, 1989

[51] Int. Cl.$^5$ .............................................. A61F 5/40
[52] U.S. Cl. .................................. 128/94; 128/87 C
[58] Field of Search .................... 128/77, 78, 87 R, 88, 128/94; 2/44, 45

[56] References Cited

U.S. PATENT DOCUMENTS

| | | | |
|---|---|---|---|
| 3,103,216 | 9/1963 | Scott | 128/94 |
| 3,404,680 | 10/1968 | Gutman et al. | 128/94 |
| 3,433,221 | 3/1969 | Kendall et al. | 128/94 |
| 3,906,944 | 9/1975 | Christen | 2/45 |
| 4,188,944 | 2/1980 | Augustyniak | 128/94 |
| 4,437,459 | 3/1984 | Slavetskas | 128/94 |
| 4,446,858 | 5/1984 | Verter | 128/165 |
| 4,476,859 | 10/1984 | Kloepfer | 128/87 B |
| 4,598,703 | 7/1986 | Lindemann | 128/94 |
| 4,784,128 | 11/1988 | Scheuermann | 128/94 |

Primary Examiner—Mickey Yu
Assistant Examiner—Charles H. Sam
Attorney, Agent, or Firm—Mathews, Woodbridge & Collins

[57] ABSTRACT

A hemi-arm sling incorporates a resilient and adjustable abduction control strap to provide support to the affected arm and shoulder area. The cuff portion of the sling is also adjustable and includes an arm engaging section and a shoulder engaging section. A chest strap attached to the shoulder engaging section wraps around the back of the patient, under the axilla of the unaffected arm, across the chest and is attached to a ring connected to the front of the cuff. The adjustable, resilient abduction control strap is fastened to the rear of the cuff at one end and is selectively attachable to the rear portion of the chest strap at the other. Mateable hook and loop material is employed to connect the abduction control strap to the rear of the chest strap. The same mateable material is employed to attach the chest strap to the ring on the front of the cuff. The hemi-arm sling is employable in rehabilitation programs to prevent dislocation of the shoulder.

7 Claims, 3 Drawing Sheets

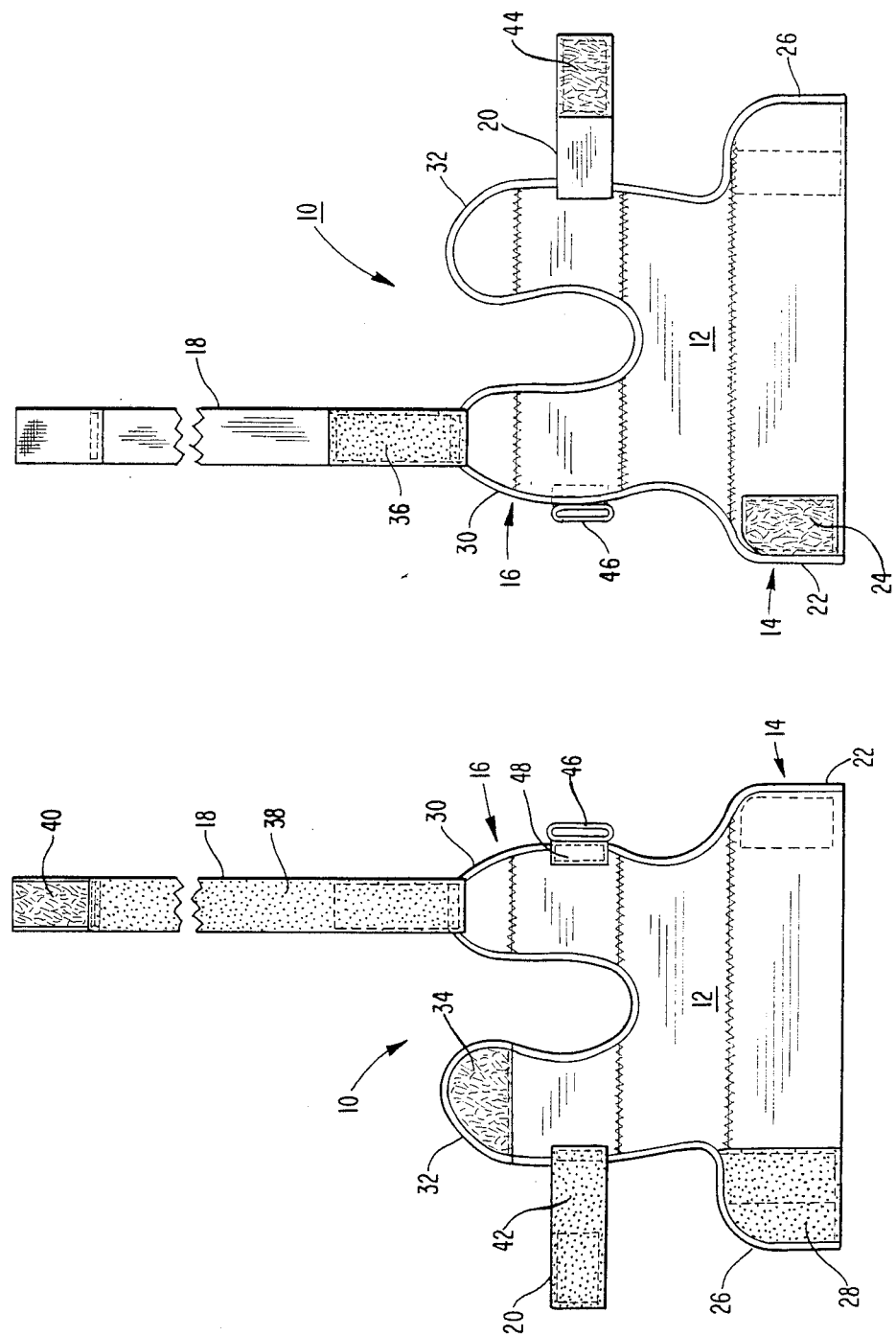

HEMI-ARM SLING WITH ABDUCTION CONTROL STRAP

BACKGROUND OF THE INVENTION

1. Field of the Invention

The invention relates to a hemi-arm sling having a resilient, adjustable abduction control strap.

2. Related Art

A variety of arm and shoulder slings are known in the prior art.

U.S. Pat. No. 4,446,858 describes an arm and shoulder brace in which the arm is supported by a strap that passes under the unaffected shoulder. Similar structures describing a strap passing under the arm of the unaffected shoulder are described in U.S. Pat. Nos. 3,404,680 and 4,188,944.

U.S. Pat. No. 4,598,703, entitled "HEMI-ARM SLING" was issued on July 8, 1986 to Peer Lindemann, the inventor of the present invention. The device described therein is held in place by an axilla loop strap encircling the unaffected shoulder. A D-ring on the back of the sling serves to permit the various straps to adjust with respect to each other. U.S. Pat. No. 4,476,859 was cited in U.S. Pat. No. 4,598,703. That patent describes a cuff that encircles the affected arm and a loop attachable by Velcro ®-like material which goes over the affected shoulder. A cross body strap is secured over the clavicle of the unaffected shoulder, however, there does not appear to be any provision for abduction control.

U.S. Pat. No. 4,437,459 discloses an additional strap that attaches to a cross body strap. U.S. Pat. No. 4,784,128 discloses a criss cross shoulder-joint bandage in which the cross portions are stitched together.

Insofar as understood, none of the prior art teaches or suggests a hemi-arm sling having the same structure and and abduction control as the present invention.

SUMMARY OF THE INVENTION

Briefly described the invention comprises a hemi-arm sling which includes a resilient and adjustable abduction control strap. The cuff portion includes an arm engaging section and a shoulder engaging section. Flaps including mateable material on the arm engaging section permit the cuff to encircle the affected arm snugly. Similarly, flaps on the shoulder engaging section include mateable material to keep the cuff in position. A chest strap attached to the posterior portion of the shoulder engaging section passes across the back of the patient, under the axilla of the unaffected arm and attaches to a ring permanently affixed to the anterior portion of the shoulder engaging section. An adjustable, resilient abduction control strap is also permanently attached at one end to the posterior portion of the shoulder engaging section of the cuff, but below the point at which the chest strap is mateably attached. The free end of the abduction control strap is attachable with Velcro ®-like material to any location on the back of the chest strap. Accordingly, it is possible to infinitely control the amount and direction of abduction control force exerted on the cuff.

The invention may be more fully understood by reference to the following drawings.

BRIEF DESCRIPTION OF THE DRAWINGS

FIG. 1 is a top plan exterior view of the preferred embodiment of the invention shown in the flat state for use on an affected right arm and shoulder.

FIG. 2 is a bottom plan interior view of the preferred embodiment illustrated in FIG. 1.

DETAILED DESCRIPTION OF THE INVENTION

Figure 3A:
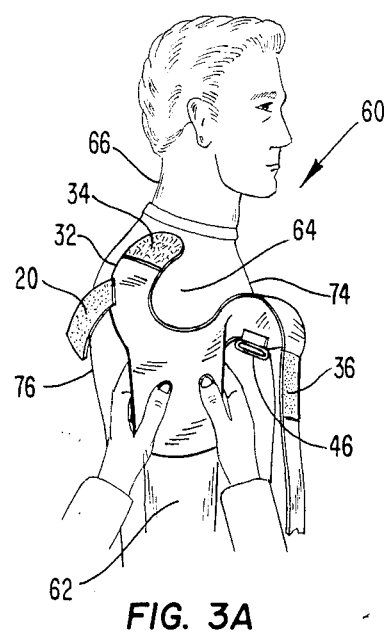
FIG. 3A illustrates the first step of attaching the hemi-arm sling to a patient in which the arm engaging section of the cuff is attached to the upper part of the affected arm.

During the course of this description, like numbers will be used to identify like elements according to the different views which illustrate the preferred embodiment of the invention 10.

The basic structure of the invention 10 is shown in detail in FIGS. 1 and 2. The hemi-arm sling essentially comprises four (4) sections, namely an adjustable cuff 12 including an arm engaging section 14, a shoulder engaging section 16, a chest strap 18, and an abduction control strap 20.

The arm engaging section 14 of cuff 12 includes an anterior flap 22 having hook type Velcro ® material 24 thereon and a posterior flap 26 having loop type material 28 thereon for selective engagement with the hook type material 24 on the anterior flap 22.

The shoulder engaging section 16 of cuff 12 includes an anterior flap 30 and a posterior flap 32 having hook type Velcro ® material 34 thereon. The shoulder engaging section 16 forms a saddle over the acrimonium of the affected shoulder 64 of the patient 60 as will be described later.

The interior side of the chest strap 18 includes a portion 36 having hook type Velcro ® material thereon. Hook type mateable material 36 is adapted to selectively engage with the hook type material 34 on the posterior flap 32 of the shoulder engaging section 16. The exterior surface of chest strap 18 includes a long section of loop type Velcro ® material 38 and a short section at the distal end thereof including hook type Velcro ® material 40.

Abduction control strap 20 includes loop type material 42 on the exterior thereof and type material 44. The abduction control strap 20 is preferably attached at one end to the posterior flap 32 of the shoulder engaging section 16 at a point below where the upper portion 36 of the chest strap 18 mates with the hook type material 34.

A ring 46 is attached by patch 48 to the posterior flap 32 of shoulder engaging section 16. Chest strap 18 is attachable to the ring 46 by passing the strap 18 through the opening in the ring 46 and then mating the hook type material 40 at the end with the loop type material 38.

The method by which the invention 10 is attached to a patient 60 is illustrated in detail in four basic steps illustrated in FIGS. 3A through 3D. In this case the invention 10 comprises a right arm sling which is intended to provide support to the affected arm 62 and affected shoulder 64 of a patient 60. While the invention is shown in the context of a right arm sling, it will be appreciated that the invention could be used on a left arm if the major elements of the invention were suitably reversed in a mirror-like manner.

The first step of attaching the hemi-arm sling 10 to a patient 60 is illustrated in FIG. 3A. As shown in FIG. 3A the anterior and posterior flaps 22 and 26, respectively, are wrapped around the affected arm 62 of the patient 60 so that hook material 24 overlaps and matingly engages with loop material 28. The fit should be snug but not so tight as to cut off circulation.

Figure 3B:
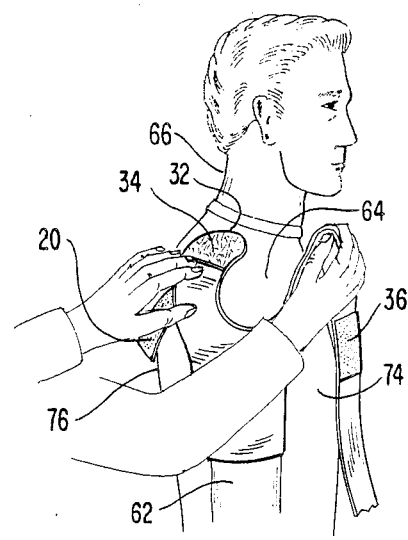
FIG. 3B illustrates the second step of attaching the hemi-arm sling to a patient in which the shoulder engaging portion of the cuff is attached over the shoulder of the affected arm.

The second step of attaching the hemi-arm sling 10 to a patient 60 is illustrated in FIG. 3B. The posterior shoulder flap 32 is held in position with hook type mateable material 34 placed on top of the scapula of the affected shoulder 64. The anterior shoulder flap 30 and chest strap 18 are brought across and over the mateable material 34 so that the loop type material 36 on chest strap 18 firmly and comfortably engages with the hook type material 34.

Figure 3C:
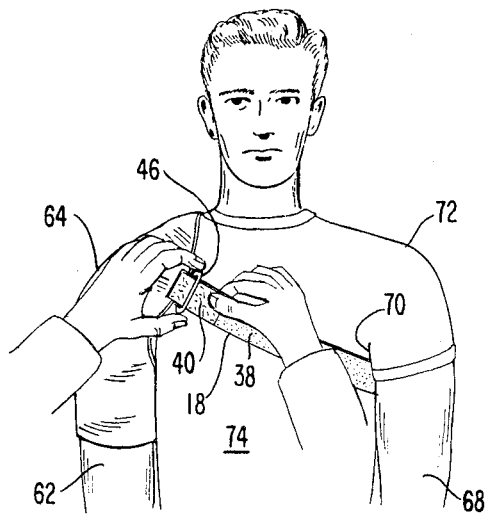
FIG. 3C illustrates the third step of attaching the hemi-arm sling to a patient in which the chest strap is passed across the back of the patient, under the axilla of the unaffected arm, across the front of the patient and is attached to a ring on the anterior portion of the cuff.

As shown in FIG. 3C, the third step of attaching the hemi-arm sling 10 is to pass the chest strap 18 across the back 76 of the patient 60, under the axilla 70 of the unaffected arm 68, across the front 74 and through the opening in ring 46. The strap 18 is preferably drawn snugly through the ring 46 until the tension is proper. The strap 18 is then doubled back on itself so that the hook type material 40 on the exterior of chest strap 18 engages with the loop type material 38.

Figure 3D:
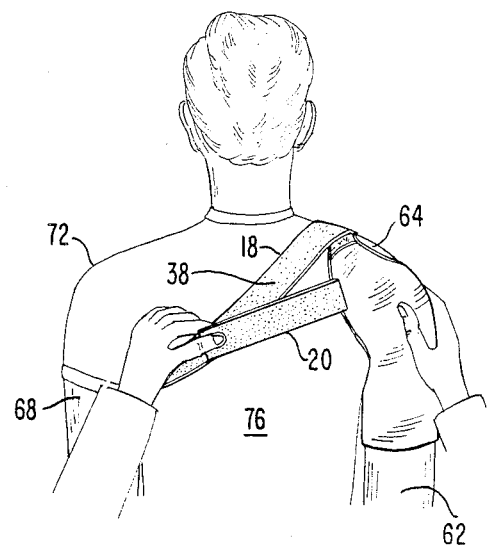
FIG. 3D illustrates the fourth and last step of attaching the invention to a patient in which the abduction control strap is adjusted for tension and direction and then firmly attached to the back of the chest strap.

The fourth and last step of attaching the hemi-arm sling 10 to the patient 60 is illustrated in FIG. 3D. The abduction control strap 20 is initially drawn tightly so as to bring the scapula of the affected shoulder 64 upwards and rearwards into the proper position. The direction, i.e. vector, of the force applied to the affected shoulder 64 is controlled by the location where the hook type material 44 lands on the loop type material 38 of the chest strap 18. The amount of tension is controlled by the resilience of the abduction control strap 20 and the location along the length of hook type material 44 that the strap is placed at. Accordingly, both the direction and force applied by abduction control strap 20 can be infinitely controlled and selectively varied.

Figure 4B:
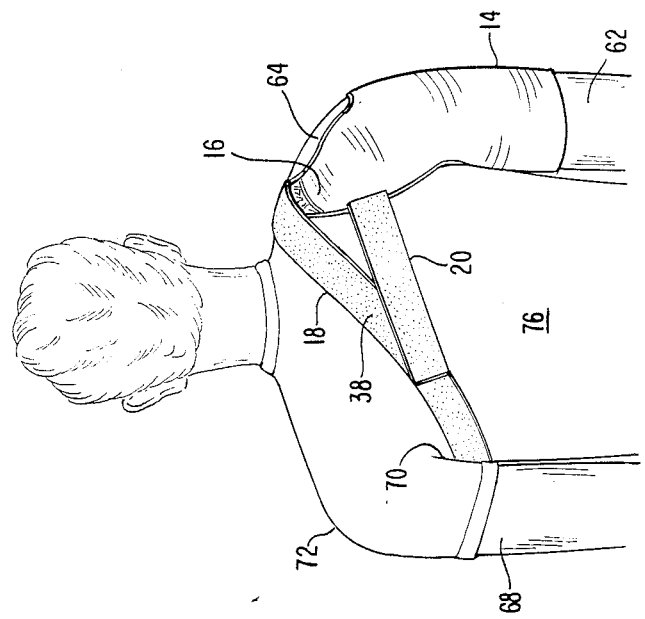
FIG. 4B is a rear view of the hemi-arm sling properly worn by a patient shown with the abduction control strap engaged.
Figure 4A:
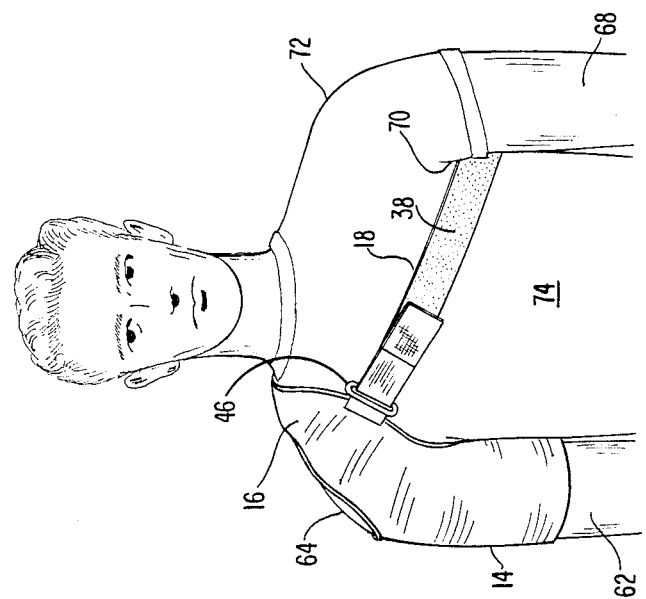
FIG. 4A is a front view of the hemi-arm sling properly worn by a patient.

FIG. 4A is a front view of the patient 60 showing the hemi-arm sling 10 in its properly worn mode. FIG. 4B shows the hemi-arm sling 10 illustrated in FIG. 4A from the back 76 of the patient 60. As previously described, when the hemi-arm sling 10 is properly fitted and adjusted on the patient 60 with the proper amount of tension applied in the right direction, the affected shoulder area 64 of the patient 60 is lifted upward and moved circumferentially rearward to prevent dislocation.

The chest strap 18 and the abduction control strap 20 according to the preferred embodiment 10 consist of resilient materials such as elasticized hook and loop manufactured by MFC. The hook type mateable materials 24, 40 and 44 as well as the loop type mateable materials 28, 36, 38 and 42 are preferably Velcro ® materials such as elasticized hook and loop manufactured by MFC. Hook and loop fasteners sold under the trademark Velcro ® are representative of the fasteners which may be used. The material comprising the cuff 12 is preferably an elastic latex impregnated material manufactured by MFC.

In addition to being able to infinitely and comfortably adjust the amount of abduction control, the present invention can be worn comfortably under clothing which is desirable for cosmetic purposes and is also useful for the treatment of sports injuries.

The preferred embodiment of the invention described in FIGS. 1–4B is shown for preventing injury to the right arm. It will also be understood that the invention can be used to provide support to the left upper arm 68 and shoulder 72 if the elements of the invention 10 are reversed in a mirror-like fashion.

The invention 10 can be employed in a therapeutic fashion to assist patients 60 who already have shoulder dislocations. The hemi-arm sling 10 can also be employed in a prophylactic manner to prevent patients 60 from injuring themselves. This is especially useful for patients who might be stroke victims because paraplegics and quadraplegics have a tendency to dislocate their shoulders due to lack of sufficient muscle tone and control.

While the invention has been described with reference to the preferred embodiment thereof, it will be appreciated by those of ordinary skill in the art that modifications can be made to the structure and elements of the invention without department from the spirit and scope thereof.

I claim:
1. A hemi-arm sling apparatus comprising:
a cuff including an adjustable arm engaging section and an adjustable shoulder engaging section attached to said adjustable arm engaging section, said arm engaging section of said cuff including a first flap having a first mateable material thereon and a second flap having a second mateable material thereon for engagement with said first mateable material, said shoulder engaging section including a first flap having a first mateable material thereon and a second flap having a second mateable material thereon for engagement with said first mateable material;
a resilient chest strap having a first end attached to said cuff and a second end;
a ring attached to said cuff for engaging the second end of said resilient chest strap; and,
adjustable abduction control means attached at one end to said cuff and attachable at the other end to said chest strap, said abduction control means comprising a resilient strap and including a first mateable material thereon for engaging with a second mateable material on said chest strap,
wherein one of said first and second mateable materials comprises a hook material and the other of said mateable materials comprises a loop material for engaging said hook material.

2. A hemi-arm sling apparatus comprising:
a cuff including an adjustable arm engaging section and an adjustable shoulder engaging section attached to said adjustable arm engaging section;

said adjustable arm engaging section of said cuff including a first flap and a second flap;

arm engaging section flap attachment means for selectively attaching said first flap of said arm engaging section to said second flap of said arm engaging section;

said shoulder engaging section including a first flap and a second flap;

shoulder engaging section flap attachment means for selectively attaching said first flap of said shoulder engaging section to said second flap of said shoulder engaging section;

a chest strap having a first end attached to said cuff and a second end;

a ring attached to said cuff for engaging the second end of said chest strap;

an adjustable abduction control strap attached at one end to said cuff and attachable at the other end to said chest strap; and, abduction control strap attachment means for selectively attaching said abduction control strap to said chest strap at a point on said chest strap intermediate the location where said chest strap is attached to said cuff and where it is attached to said ring.

3. The apparatus of claim 2 wherein said chest strap and said abduction control strap are resilient.

4. The apparatus of claim 3 wherein said abduction control strap attachment means comprises hook and loop mateable materials.

5. The apparatus of claim 4 wherein said shoulder engaging section flap attachment means comprises hook and loop mateable materials.

6. The apparatus of claim 5 wherein said arm engaging section flap attachment means comprises hook and loop mateable materials.

7. A method for attaching a hemi-arm sling to a patient, said hemi-arm sling including a cuff having an affected arm engaging section, and an affected shoulder engaging section connected to said arm engaging section, said affected shoulder engaging section including a first and a second flap that are attachable to each other, a ring attached to said cuff, a chest strap attached at one end to said cuff and attachable at the other end thereof to said ring, and an abduction control strap attached at one end to said cuff and attachable at the other end thereof to said chest strap, the method comprising the steps of:

(a) attaching said arm engaging section to the affected arm of the patient;

(b) attaching the first and second flaps of said shoulder engaging section to each other over the affected shoulder of the patient;

(c) passing said chest strap around the back of said patient, under the axialla of the unaffected arm of the patient, and attaching the free end of said chest strap to said ring on said cuff;

(d) applying tension on said abduction control strap to rotate the affected shoulder upward and rearwardly; and, (e) attaching the abduction control strap to the chest strap at a point intermediate the locations where said chest strap is attached to said cuff and to said ring thereby maintaining tension on the abduction control strap and therefore on the affected shoulder of the patient.

* * * * *